United States Patent [19]
Samukov et al.

[11] Patent Number: 5,616,788
[45] Date of Patent: Apr. 1, 1997

[54] $N_\alpha$-2-(4-NITROPHENYLSULFONYL) ETHOXYCARBONYL-AMINO ACIDS

[75] Inventors: Vladimir V. Samukov; Aydar N. Sabirov; Pavel I. Pozdnyakov, all of Novosibirsk, Russian Federation

[73] Assignee: Hyundai Pharm. Ind. Co., Ltd., Seoul, Rep. of Korea

[21] Appl. No.: 595,381

[22] Filed: Feb. 1, 1996

[30] Foreign Application Priority Data

Feb. 15, 1995 [RU] Russian Federation ... 95102102/04(00

[51] Int. Cl.⁶ .................................................. C07C 315/00
[52] U.S. Cl. .......................... 562/430; 560/13; 549/390; 548/338.5; 548/495
[58] Field of Search ................ 562/430; 560/13; 549/390; 548/338.5, 495

[56] References Cited

PUBLICATIONS

Smukov, V.V., Tetrahedron Letters, vol. 35, No. 42 p. 7821–7824 (1994) (Exhibit 1) Oct. 17, 1994.
Chem Abstracts 115:72199, Schielen et al Date 1991.

*Primary Examiner*—Samuel Barts
*Attorney, Agent, or Firm*—John P. White

[57] ABSTRACT

Protected amino acid derivatives of the general formula

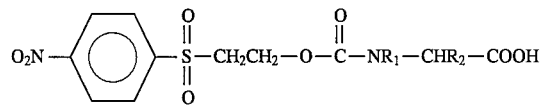

wherein $R_1$ represents hydrogen atom, and $R_2$ represents hydrogen, methyl, isopropyl, 1-methylpropyl, 2-methylpropyl, tert-butoxymethyl, 1-tert-butoxyethyl, 2-methylthioethyl, benzyl, carboxamidomethyl, 2-carboxamidoethyl, tert-butoxycarbonylmethyl, 2-(tert-butoxycarbonyl)ethyl, 4-(tert-butoxycarbamido)butyl, 4-tert-butoxybenzyl, indolyl-3-methyl, S-(triphenylmethyl)thiomethyl, 1-(triphenylmethyl)imidazolyl-4-methyl, 3-($N^G$-mesitylenesulfonyl)guanidinopropyl, N-xanthylcarboxamidomethyl, 2-(N-xanthylcarboxamido)ethyl or S-(acetamidomethyl)thiomethyl; or $R_1$ and $R_2$ together represent propylene radical. Methods for the preparation of said derivatives are provided, and a process for solid phase peptide synthesis using said derivatives is described.

4 Claims, No Drawings

$N_\alpha$-2-(4-NITROPHENYLSULFONYL) ETHOXYCARBONYL-AMINO ACIDS

BACKGROUND OF THE INVENTION

The field of the invention concerns protected amino acid derivatives for solid phase peptide synthesis, namely, $N_\alpha$-2-(4-nitorphenylsulfonyl)ethoxycarbonyl-amino acids having the general formula I:

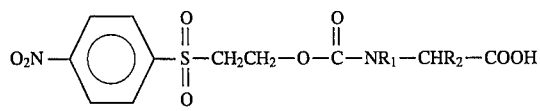

wherein $R_1$ represents hydrogen atom, and $R_2$ may represent hydrogen, methyl, isopropyl, 1-methylpropyl, 2-methlypropyl, tert-butoxymethyl, 1-tert-butoxyethyl, 2-methylthioethyl, benzyl, carboxamidomethyl, 2-carboxamidoethyl, tert-butoxycarbonylmethyl, 2-(tert-butoxycarbonyl)ethyl, 4-(tert-butoxycarbamido)butyl, 4-tert-butoxybenzyl, indolyl-3-methyl, S-(triphenylmethyl)thiomethyl, 1-(triphenylmethyl)imidazolyl-4methyl, 3-($N^G$-mesitylenesulfonyl)guanidinopropyl, N-xanthylcarboxamidomethyl, 2-(N-xanthylcarboxamido)ethyl or S-(acetamidomethyl)thiomethyl.

or $R_1$ and $R_2$ together represent propylene radical, employed as $N_\alpha$-protected amino acid derivatives for solid phase peptide synthesis.

Solid phase peptide synthesis is widely employed for the preparation of biologically active peptides which are used in medical and biological research and also as active substances in pharmacy, veterinary and diagnostics.

The essence of solid phase peptide synthesis can be outlined as a stepwise elongation of a peptide chain by means of repeated cycles of chemical reactions, beginning from the first C-terminal amino acid attached to an unsoluble carrier. During the course of the synthesis target products of all reactions remain bound to the carrier, whereas excessive reactants and side-products are removed by filtration and washing of the carrier.

In order to perform the solid phase synthesis of a peptide, the first amino acid (C-terminal of the target amino acid squence) with the protected α-amino group is linked covalently to an unsoluble polymeric carrier through the free α-carboxyl group by ester or amide bond formation. Then $N_\alpha$-protective group is selectively cleaved from thus obtained $N_\alpha$-protected aminoacyl-polymer, and the aminoacyl-polymer with the free α-amino group is formed. This polymer is further acylated with the next $N_\alpha$-protected amino acid, thus giving $N_\alpha$-protected dipeptidyl-polymer. Such synthetic cycles, which consist of $N_\alpha$-protection cleavage and of subsequent acylation of free amino group with following $N_\alpha$-protected amino acid, are repeated until the assembly of target amino acid sequence is completed.

In practical solid phase synthesis large molar excesses(2 to 10-fold) of acylating reagents are usually employed to assure complete conversion, therefore, all reactive groups in side chains of the amino acids, such as amino, carboxyl, hydroxyl, thiol, guanidino groups, should be blocked with appropriate protective groups. The protective groups for this purpose must be selected carefully to provide reliable and permanent protection of the side chains under conditions of peptidyl-polymer acylations and during the cleavage of temporary $N_\alpha$-protection. On the other hand, these side-chain protective groups must provide the opportunity to deprotect the synthesized peptide in one or two stages quantitatively and without damage of its structure. In most cases the peptidyl-polymer linkage also should be cleaved simultaneously. It is evident that the structure and the chemical properties of permanent protective groups for side-chains of amino acids are determined not only by the nature of reactive function to be protected but in a great extent by the structure and the chemical properties of the employed temporary $N_\alpha$-protective group. Therefore, temporary $N_\alpha$-protection is the key element of the whole strategy of solid phase peptide synthesis.

Well known and widely used in solid phase peptide synthesis are $N_\alpha$-tert-butoxycarbonyl amino acids(Boc-amino acids) described for this purpose by R. B. Merrifield in *Biochemistry*, 1964, V. 3, p. 1385. tert-Butoxycarbonyl-(Boc) group can be cleaved by the action of acidic reagents of medium strength, such as, for example, trifluoroacetic acid and its solutions in chlorinated hydrocarbons, solutions of hydrogen chloride in organic solvents, boron trifluoride/diethyl ether complex and some other acids, with the formation of isobutylene and carbon dioxide.

Together with temporary $N_\alpha$-Boc-protection for the permanent blocking of side chains protective groups are employed, which are stable during $N_\alpha$-Boc cleavage but can be cleaved by more strong acidic reagents with the simultaneous fission of peptidyl-polymer bond. Known reagents used for this purpose are liquid hydrogen fluoride, trifuoromethanesulfonic acid and their mixtures with anisole, thioanisole, dimethylsulfide. The main drawback of the synthetic strategy with the use of temporary $N_\alpha$-Boc-protection is the application of acidolysis for the cleavage of both temporay and permanent protective groups, that cannot provide complete stability of the permanent protection. As the length of synthesized peptide grows, permanent protective groups undergo cumulative action of acidic reagents during Boc cleavage steps, that can result in partial loss of these groups and accumulation of side-products. Apart of this, the final treatment of assemblied peptidyl-polymer with superacidic reagents can cause partial destruction of the target peptide. It also should be mentioned that extremely hazardous propeties of superacids require special equipment and appropriate safety measures during handing.

To aviod the use of superacidic reagents for the final peptide deprotection, several highly acid-sensitive groups were proposed more recently as a temporary $N_\alpha$-protection, which are considered to be compatible to permanent side-chain protection of so-called tert-butyl type cleavable by acidic reagents of medium strength. An example of such $N_\alpha$-protective group is 1-(3,5-di-tert-butylphenyl)-1-methyl-ethoxycarbonyl(t-Bumeoc)group, which is described in *Collect. Czech. Chem. Commun.*, 1992, V. 57, p. 1707. $N_\alpha$-t-Bumeoc-group is cleaved by 1% trifluoroacetic acid in dichloromethane and can be used together with permanent protective groups of t-butyl type cleavable by neat trifluoroacetic acid or its concentrated solutions. In this case the employment of superacids is excluded but general principle of differential acidolysis still remains unchanged.

A different approach to the strategy of solid phase peptide synthesis is outlined by R. B. Merrifield in *Science*, 1986, V. 232, p. 341. This approach, called "orthogonality principle", is based on the assumption that temporary and permanent protective groups should be removable by totally distinct reagents according to totally distinct chemical mechanisms, so that temporary $N_\alpha$-protection could be cleaved with absolute selectivity providing full preservation of permanent protection, and vice versa. At present time the "orthogonality principle" is commonly accepted as a guideline for the development of efficient strategies of solid phase peptide synthesis.

As an example of implementation of the "orthogonality principle" the employment of $N_\alpha$-dithiasuccinylamino acids(Dts-amino acids) in solid phase synthesis is described in *Int. J. Peptide and Protein Res.*, 1987, V. 30. p. 740. $N_\alpha$-Dithiasuccinyl(Dts) protective group is quite resistant to acidic reagents of medium strength and is cleaved smoothly by thiol reagents in neutral media with the liberation of amino group and formation of carbon thiooxide. Application of Dts-amino acids in practical synthesis is still limited due to the lack of effective methods for their preparation.

The most known and widely employed strategy of solid phase synthesis, which corresponds to the "orthogonality principle", is based on the use of $N_\alpha$-9-fluorenylmethoxycarbonylamino acids(Fmoc-amino acids), as described by C. D. Chang and J. Meienhofer in *Int. J. Peptide and Protein Res.*, 1975, V. 11, p. 246. $N_\alpha$-9-Fluorenylmethoxycarbonyl(Fmoc) group is resistant to to acidic reagents and is cleaved according to the β-elimination mechanism by organic bases in aprotic solvents, for example, by morpholine diethylamine, piperazine, or piperidine in dimethylformamide(DMF) or dichloromethane, amino group being liberated and dibenzofulvene together with $CO_2$ being formed. In solid phase synthesis the cleavage of Fmoc group is preferably performed by the treatment of $N_\alpha$-protected peptidyl-polymer with 20 to 50% piperidine in DMF during 10 to 30 min. Said conditions allow to use permanent acid sensitive protection of t-butyl type together with temporary $N_\alpha$-Fmoc-protection, thus providing the "othogonality" of the synthetic strategy.

$N_\alpha$-Fmoc-amino acids are widely used in manual solid phase peptide syntyesis, as well as in automatic and semiautomatic synthesizer of all types. However, it should be noted that extreme base sensitivity of $N_\alpha$-Fmoc-protection and some its unstability in neutral aprotic solvents require to control carefully acylation conditions and also the purity of empolyed solvents. Special care sholud be taken when $N_\alpha$-Fmoc-amino acids are used for the synthesis of peptides exceeding 30 residues in length. Besides, relatively high cost of production prevents the use of Fmoc-derivatives in large scale peptide preparations.

SUMMARY OF THE INVENTION

It is, therefore, desirable to develop new $N_\alpha$-protected amino acid derivatives which may be useful for the development of efficient strategies in solid phase peptide synthesis. An object of the present invention is to provide new amino acids derivatives, more particularly, $N_\alpha$-2-(4-nitrophenylsulfonyl)ethoxycarbony-amino acids($N_\alpha$-Nsc-amino acids)having the general formula I:

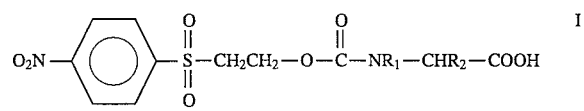

wherein $R_1$ represents hydrogen atom, and $R_2$ may represent hydrogen, methyl, isopropyl, 1-methylpropyl, 2-methylpropyl, tert-butoxymethyl, 1-tert-butoxyethyl, 2-methylthioethyl, benzyl, carboxamidomethyl, 2-carboxamidoethyl, tert-butoxycarbonylmethyl, 2-(tert-butoxycarbonyl)ethyl, 4-(tert-butoxycarbamido)butyl, 4-tert-butoxybenzyl, indolyl-3-methyl, S-(triphenylmethyl)thiomethyl, 1-(triphenylmethyl) imidazolyl-4-methyl, 3-($N^G$-mesitylenesulfonyl)guanidinopropyl, N-xanthylcarboxamidomethyl, 2-(N-xanthylcarboxamido)ethyl or S-(acetamidomethyl)thiomethyl;

or $R_1$ and $R_2$ together repersent propylene radical, which can be employed as $N_\alpha$-protected amino acid derivatives in solid phase peptide synthesis.

Another object of the present invention is to provide methods for the preparation of said $N_\alpha$-Nsc-amino acids. Still another object of the invention is to provide a process for solid phase peptide synthesis using the $N_\alpha$-Nsc-amino acids. These and other object of the present invention will be apparent from the following description.

DETAILED DESCRIPTION OF THE INVENTION $N_\alpha$-Nsc-amino acids of the present invention(I) can be prepared by the treatment of amino acids of the general formula II, wherein $R_1$ and $R_2$ represent meanings given for formula I, with 2-(nitrophenylsulfonyl)chloroformate III in mixed aqueous/organic solvent in the presence of base and at the temperature from 0° to 40° C., preferably from 0° to 20° C. (Scheme 1).

Scheme 1

$HNR_1-CHR_2-COOH +$

II

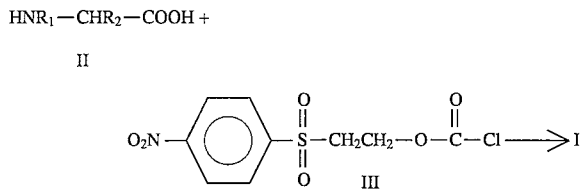

Chloroformate III is introduced into the reaction in amounts from 0.5 to 1.5 molar equivalents, preferably from 0.7 to 0.9, as related to amino acid. As an organic component of the solvent any aprotic organic solvent may be used which is capable to disslove the acylating reagent and is mixible with water, for example, acetonitrile, DMF, tetrahydrofuran or dioxane. A base may be organic or Inorganic base, for example, sodium or potassium carbonate, magnesium or calcium oxide, triethylamine, N-methylmorpholine.

According to another method of the present invention, amino acids of the general formula II are firstly converted into N,O-bis-trimethylsilyl derivatives IV using methods known in the art and then treated with chloroformate III in anhydrous organic solvent, for example, dichloromethane. After aqueous hydrolysis of intermediate trimethylsilyl derivatives desirable $N_\alpha$-Nsc-amino acids I are obtained in a free form(Scheme 2).

Scheme 2

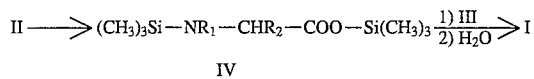

Derivatives of the formula I, wherein $R_1$ is hydrogen, and $R_2$ represents N-xanthylcarboxamidomethyl or 2-(N-xanthylcarboxamido)ethyl, may be prepared by the reaction of the derivatives of the formula I, wherein $R_1$ is hydrogen, and $R_2$ represents carboxamidomethyl or 2-(carboxamido)ethyl, with xanthydrol in aprotic organic solvent in the presence of acid. As a solvent DMF may be used, and preferable acid is organic acid, for example, trifluoroacetic, methanesulfonic or p-toluenesulfonic acid.

It is seen from molecular formula that compounds I have an asymmetric α-carbon atom(except for compound where $R_1=R_2=H$). Because α-carbon atom does not participate in reactions employed for the preparation of compounds I, so the configuration of this chiral center existing in starting amino acids II is retained in resulting $N_\alpha$-Nsc-derivatives I. Therefore it is obvious that the methods of the present invention can be used for the preparation of $N_\alpha$-Nsc-amino acids I in any chiral form(L or D), as well as racemic compounds, depending on the configuration of the strating compound II.

Meanings of $R_1$ and $R_2$ substituents in derivatives of the formula I according to the present invention correspond to structures of sids chains of naturally occurring amino acids containing or not containing protective groups known in the art, mostly the groups of tert-butyl type or similar to them in relation to the cleavage conditions(Table 1).

obtained: A variety of polymers may be used as a polymeric carrier, such as cross-linked or macroporous polystyrene, cross-linked poly-N,N-dimethylacrylamide in granular form or as a composite with kieselguhr, cross-linked dextranes, celluloses, papers and other polymers known in the art and employed for this purpose.

For the attachment of the first $N_\alpha$-Nsc-amino acid the polymeric carrier should contain appropriate anchor groups. In most instances anchor groups are preferable which provide the cleavage of synthesized peptide from polymeric carrier with the liberation of C-terminal carboxyl or carboxamide group during the treatment of peptidyl-polymer with acidic reagents, such as trifluoroacetic acid and its solutions or hydrogen chloride solutions in organic solvent.

TABLE 1

Meaning of $R_1$ and $R_2$ substituents in compounds I

| No | $R_1$ | $R_2$ | Anino acid | Abbreviation |
|---|---|---|---|---|
| I-1 | H | H | Glycine | Nsc—Gly—OH |
| I-2 | H | Methyl | Alanine | Nsc—Ala—OH |
| I-3 | H | Isopropyl | Valine | Nsc—Val—OH |
| I-4 | H | 1-Methylpropyl | Isoleucine | Nsc—Ile—OH |
| I-5 | H | 2-Methylpropyl | Leucine | Nsc—Leu—OH |
| I-6 | H | tert-Butoxymethyl | O-tert-Butyl-serine | Nsc—Ser(tBu)—OH |
| I-7 | H | 1-tert-Butoxymethyl | O-tert-Butyl-threonine | Nsc—Thr(tBu)—OH |
| I-8 | H | 2-Methylthioethyl | Methionine | Nsc—Met—OH |
| I-9 | H | Benzyl | Phenylalanine | Nsc—Phe—OH |
| I-10 | H | Carboxamidomethyl | Asparagine | Nsc—Asn—OH |
| I-11 | H | 2-Carboxamidoethyl | Glutamine | Nsc—Gln—OH |
| I-12 | H | tert-Butoxycarbonyl-methyl | Aspartic acid β-tert-butyl ester | Nsc—Asp(OtBu)—OH |
| I-13 | H | 2-(tert-Butoxycarbonyl)ethyl | Glutamic acid γ-tert-butyl ester | Nsc—Glu(OtBu)—OH |
| I-14 | H | 4-(tert-Butoxycarbamido)butyl | $N_\epsilon$tert-Butoxycarbonyl-lysine | Nsc—Lys(Boc)—OH |
| I-15 | H | 4-tert-Butoxybenzyl | O-tert-Butyl-tyrosine | Nsc—Tyr(tBu)—OH |
| I-16 | H | Indolyl-3-methyl | Tryptophan | Nsc—Trp—OH |
| I-17 | H | S-(triphenylmethyl)thiomethyl | S-Triphenylmethyl-cysteine | Nsc—Cys(Trt)—OH |
| I-18 | H | 1-(Tripherrylmethyl)imidazolyl-4-methyl | Nτ-Triphenylmethyl-histidine | Nsc—His(Trt)—OH |
| I-19 | H | 3-($N^G$-Mesitilene-sulfonyl)guanidinopropyl | $N^G$-Mesitilenesulfonyl-arginine | Nsc—Arg(Mts)—OH |
| I-120 | H | N-Xanthylcarboxamido-methyl | N-Xanthyl-asparagine | Nsc—Asn(Xan)—OH |
| I-21 | H | 2-(N-Xanthylcarboxamido)ethyl | N-Xanthyl-glutamine | Nsc—Gln(Xan)—OH |
| I-22 | H | S-(Acetamidomethyl)thiomethyl | S-Acetamidomethyl-cysteine | Nsc—Cys(Acm)—OH |
| I-23 | $R_1 + R_2$ = Propylene | | Proline | Nsc—Pro—OH |

Apparently the compounds of the formula I shown in Table I represent a full set of protected proteogenic amino acid derivatives required for the synthesis of a peptide of any amino acid composition. It is also apparent that $N_\alpha$-Nsc-derivatives of amino acids carrying another types of backbone protection as well as $N_\alpha$-Nsc-derivatives of non-preoteogenic or unusual amino acids can be synthesized by the provided method.

$N_\alpha$-Nsc-amino acids T are crystalline compounds unsoluble or slightly soluble in water and soluble in polar organic solvents, stable at long-term storage at −10° to 25° C.

According to the present invention a process is provided for solid phase peptide synthesis using the $N_\alpha$-Nsc-amino acids of the formula I.

By this process the first $N_\alpha$-Nsc-amino (C-terminal of the traget amino sequence)is linked covalently to an unsoluble polymeric carrier through the free α-carboxyl group by ester or amide bond formation, $N_\alpha$-Nsc-aminoacyl-polymer being Such anchor groups for the ester type attachment may be 4-hydroxymethylphenoxyalkyl, 4-chloro- or 4-bromomethylphenoxyalkyl, α-hydroxydiphenylmethyl and other groups known in the art; for the carboxamide type attachment there may be known di- and trialkoxybenzhydrylanime groups, 4-aminomethyl-3,5-dimethoxyphenoxyalkyl group and also other known groups employed for this purpose.

Attachment of the C-terminal $N_\alpha$-Nsc-amino acid to anchor groups of polymeric carrier may be performed by the methods known in the art.

In order to cleave $N_\alpha$-protective group from the obtained $N_\alpha$-Nsc-aminoacyl-polymer, said protected aminoacyl-polymer is threated with basic reagent. Preferable basic reagents for this purpose are nitrogen bases, e.g. ammonia, morpholine, piperidine, piperazine, diethylamine, 1,8-diazabicyclo[5,4,0]undec-7-ene, 1,1,3,3-tetramethylguanidine and their solutions in aprotic organic solvents. More preferable basic reagent is 20 to 50% solution of piperidine in DMF. In this instance Nsc-group is cleaved with the formation of N-[2-(4-nitrophenylsulfonyl)ethyl]piperidine and carbon dioxide, α-amino group being liberated.

Further the aminoacyl-polymer with the free α-amino group is acylated with the next $N_\alpha$-Nsc-amino acid, thus giving $N_\alpha$-Nsc-dipeptidyl-polymer. For this purpose methods are employed known in the art and usually used for this purpose. As acylating agents may be used, for example, 4-nitrophenyl, pentachlorophenyl, pentafluorophenyl, 1-hydroxybenzotriazolyl esters of $N_\alpha$-Nsc-amino acids and other known types of active esters used in solid phase peptide synthesis; symmetric anhydrides of $N_\alpha$-Nsc-amino acids. Acylation may also be performed with $N_\alpha$-Nsc-amino acids in the presence of known coupling reagents, e.g. dicyclohexylcarbodiimide, diisopropylcarbodiimide, benzotriazolyl-1-oxy-(tris-dimethylamino)phosphonium hexafluorophosphate.

Synthetic cycles, which consist of $N_\alpha$-Nsc-group cleavage and of subsequent acylation of free amino group with following $N^\alpha$-Nsc-amino acid, are repeated until the assembly of target amino acid sequence is completed.

After the assembly of desired $N_\alpha$-Nsc-peptidyl-polymer $N_\alpha$-terminal protective group is cleaved using methods described above, then in most instances the target peptide is detached from the anchor group of the carrier with concurrent cleavage of permanent protection from side chains of amino acids. For this purpose acidic reagents may be employed known in the art for the cleavage of tert-butyl type protective groups, e.g., trifluoroacetic acid, sloutions of methanesulfonic or p-toluenesulfonic acid, containing or not containing known additives for trapping of evolved carbonium ions, for instance, water, anisole, thioanisole, dimethylsulfide, ethanedithiol- 1,2,-triisopropylsilane.

Optionally, target peptide may be deblocked without cleavage from polymeric carrier. In such instances known anchor groups should be employed which can provide an acid-resistant peptidyl-polymer linkage.

In comparison to Fmoc, Nsc-group is more resistant to basic reagents, and its cleavage rates are markedly slower under similar conditions, but the time, which is usually allocated for the cleavage of $N_\alpha$-protection according to protocols of solid phase synthesis(15–20 min), is sufficient for quantitative cleavage of $N_\alpha$-Nsc-group from protected peptidyl-polymer by the such basic reagent as 20 to 50% solution of piperidine in DMF. On the other part, increased resistance of Nsc-group to basic reagents provides its more pronounced stability in neutral and weakly basic media, which are preferably employed for performing of acylation steps.

As described above, Nsc-group may be cleaved quantitatively by basic reagents in the presence of tert-butyl type protective groups, which are resistant towards organic bases. On the other hand, Nsc-group is perfectly resistant to the action of acidic reagents usually used for the cleavage of protective groups of tert-butyl type. Thus the employment of $N_\alpha$-Nsc-amino acids of general formula I, which contain in side chains protective group preferably of tert-butyl type or similar to them in relation to cleavage conditions, allows to develop new strategies of solid phase peptide synthesis in concordance to the "orthogonality principle".

The invention will now be described by way of examples which are provided as illustration and are not intended as being limiting. All of the amino acids in the following description have L-configuration unless otherwise indicated.

EXAMPLE 1

$N_\alpha$-Nsc-Asparagine(I-10)

3.95 g of asparagine and 7.7 g of potassium carbonate were dissolved in 100 ml of water-dioxane mixture(3:1, v/v) and cooled in ice bath, then solution of 7.5 g of 2-(4-nitrophenylsulfonyl)ethyl chloroformate III in 70 ml of dioxane was added dropwise within 15 min with stirring. Cooling bath was removed and mixture was stirred for additional 20 min, then evaporated to ca. 100 ml under reduced pressure and transferred into separating funnel. 100 ml of water was added, and the resulting solution was extracted with 2×50 ml of ethyl acetate. Aqueous layer was separated, acidified to pH 2 with 40% sulfuric aicd and cooled in ice bath. After 30 min the formed precipitate was filtered off, washed extensively with ice-cold water and air-dried yielding the desired compound I-10 as a white crystalline powder(71%), For characterization see Table 2(Example 5).

EXAMPLE 2

$N_\alpha$-Nsc-Leucine(I-5)

4.92 g of leucine and 90 ml of anhydrous dichloromethane were placed into 250 ml round-bottom flask equipped with reflux condenser and dropping funnel. To the suspension 9.5 ml of chlorotrimethylsilane was added with vigorous stirring, and the mixture was heated to boiling for 1 hr. The resulting solution was cooled in ice bath, then 9.1 ml of triethylamine and 9.0 g of chloroformate III were added with stirring. The mixture was stirred for 20 min in ice bath, then for additional 1.5 hr at room temperature. The solvent was evaporated at reduced pressure, and the residue was distributed between 200 ml of ethyl acetate and 250 ml of 2.5% aqueous sodium bicarbonate. Aqueous layer was separated, washed with 50 ml of ether, acidified to pH 2 with 1N hydrochloric acid, then extracted with 3×70 ml of ethyl acetate. Combined extracts were dried with anhydrous sodium sulfate and evaporated at reduced pressure. Recrystallization of the residue from hexane-ethyl acetate gave the desired product I-5 in a form of white crystalline powder(80%). For characterization see Table 2(Example 5).

EXAMPLE 3

$N_\alpha$-Nsc-Aspartic Acid β-tert-Butyl Ester(I-12)

7.09 g of aspartic acid β-tert-butyl ester and 90 ml of anhydrous dichloromethane were placed into 250 ml round-bottom flask equipped with reflux condenser and dropping funnel. To the mixture 12.7 ml of diisopropylethylamine and then 9.5 ml of chlorotrimethylsilane were added with vigorous stirring, and the mixtire was heated to boiling for 1.5 hr. The reaction mixture was then cooled in ice bath, 9.0 g of chloroformate III was added at once, and stirring was continued for 1.5 hr at room temperature. The solvent was evaporated at reduced pressure, and the residue was distributed between 200 ml of ethyl acetate and 250 ml of 2.5% aqueous sodium bicarbonate. Aqueous layer was separated, washed with 50 ml of ether, acidified to pH 2 with 1N hydrochloric acid, then extracted with 3×70 ml of ethyl acetate. Combined extracts were dried with anhydrous sodium sulfate and evaporated at reduced pressure. Recrystallization of the residue from hexane-ethyl acetate gave the desired product I-12 in a form of which crystalline powder(86%). For characterization see Table 2(Example 5).

EXAMPLE 4

$N_\alpha$-Nsc-N-Xanthyl-Asparagine(I-20)

3.89 g of $N_\alpha$-Nsc-asparagine(I-10)and 2.6 g of xanthydrol were dissolved in 20 ml of dry DMF. To the solution 0.4 ml of methanesulfonic acid was added, and the mixture was allowed to stand for 2 days at room temperature. The resulting mixture was then poured into 100 ml of ice-cold water with mixing, the formed precipitate was filtered off, washed with water and then with ethyl acetate and ether. The crude product was dissolved in 10 ml of warm DMF, filtered and reprecipitated with ether. The precipitate was collected by filtration, washed with ether and dried in vacuo yielding the desired compound I-20 as a crystalline powder(74%). For characterization see Table 2(Example 5).

EXAMPLE 5

Properties of $N_\alpha$-Nsc-amino acids I

Shown in Table 2 are the compounds of formula I which were prepared utilizing provided methods described in detail in example 1–4. Figures in the column "Method" correspond to numbers of examples where particular methods are described. Specific optical rotations $[a]_D^{25}$ were measured on DIP-320 polarimeter(JASCO, Japan) in 10 cm cuvettes. Melting points were determined in open capillaries and were not corrected. Chromatographic mobility values $R_f$ were shown for thin-layer chromatography sheets Alufolien Kieselgel 60 $F_{254}$(Merck, Darmstadt, Germany); chloroform/methanol/acetic acid, 95:5:3, (A)and benzene/acetone/acetic acid. 100:50:3, (B), were used as developing solvents, spots were detected by UV-absorbance and/or by ninhydrin reaction. Molecular ion masses$(M+H)^+$ were measured using MS-BC-1 time-of-flight mass spectrometer with $Cf^{252}$ radiation-promoted desorption(Electron SPA, Sumy, Ukraine).

of 2,4,5-trichlorophenyl 4-hydroxymethylphenoxypropionate and 0.75 mmol of 1-hydroxybenzotriazole were added, and the suspension was shaken for 24 hrs at room temperature. Polymer was filtered off, washed with DMF, ethanol, ether and, finally, with hexane and dried in vacuo over phosphorus pentaoxide for 24 hrs.

b) Attachment of Nsc-Lys(Boc)-OH to anchor group.

The obtained polymer was swollen in 4 ml of 1,2-dichloroethane/N-methylpyrrolidine mixture(3:1), then 0.75 mmol of Nsc-Lys(Boc)-OH(I-14), 0.1 mmol of 4-dimethylaminopyridine and 0.75 mmol of dicyclohexylcarbodiimide were added. The suspension was shaken for 24 hrs at room temperature. Polymer was filtered off, thoroughly washed with chloroforrm, chloroform/methanol mixture(1:1), ethanol, ether and, finally, with hexane and dried yielding 400 mg of Nsc-Lys(Boc)-polymer.

c) Peptide assembly

Nsc-Lys(Boc )-polymer(200 mg) was placed into 10 ml polypropylene syringe equipped at the bottom with polypropylene frit. The polymer in the syringe was washed with DMF, and further synthetic cycles were performed accoring to the following operational protocol:

| | |
|---|---|
| 1. Prewash: | 33% piperidine/DMF, 4 ml; 0.5 min. |
| 2. Deblocking: | 33% piperidine/DMF, 4 ml; 15 min |
| 3. Wash: | DMF, 6 × (4 ml; 1 min) |
| 4. Acylation: | $N_\alpha$—Nsc-amino acid I, 0.5 mmol; benzotriazolyl-1-oxy-(trisdimethylamino)phosphonium hexafluorophosphate, |

TABLE 2

Properties of $N_\alpha$—Nsc-amino acids I

| Entry | Compound | Method | $[a]_D^{25}$ (c1, DMF) | mp, °C. | $R_f$(A) | $R_f$(B) | Molecularion, $(M + H)^{30}$ Calcd | Found |
|---|---|---|---|---|---|---|---|---|
| I-1 | Nsc—Gly—OH | 2 | — | 152–154 | 0.40 | 0.21 | 333.30 | 333.4 |
| I-2 | Nsc—Ala—OH | 2 | −25.6° | 134–136 | 0.53 | 0.35 | 347.32 | 347.4 |
| I-3 | Nsc—Val—OH | 2 | −12.0° | 72–74 | 0.62 | 0.50 | 375.38 | 375.4 |
| I-4 | Nsc—Ile—OH | 2 | −13.0° | 120–121 | 0.62 | 0.52 | 389.41 | 389.6 |
| I-5 | Nsc—Leu—OH | 2 | −33.0° | 160–162 | 0.68 | 0.42 | 389.41 | 389.7 |
| I-6 | Nsc—Ser(tBu)—OH | 3 | +3.3° | 109–111 | 0.68 | 0.46 | 419.43 | 418.9 |
| I-7 | Nsc—Thr(tBu)—OH | 3 | −9.0° | 64–66 | 0.68 | 0.50 | 433.46 | 433.2 |
| I-8 | Nsc—Met—OH | 2 | −28.7° | 88–90 | 0.65 | 0.37 | 407.47 | 406.9 |
| I-9 | Nsc—Phe—OH | 2 | −23.0° | 160–163 | 0.66 | 0.40 | 423.42 | 423.3 |
| I-10 | Nsc—Asn—OH | 1 | −1.3° | 205–207 | 0.05 | 0.05 | 390.35 | 390.2 |
| I-11 | Nsc—Gln—OH | 1 | −9.7° | 192–194 | 0.10 | 0.05 | 404.38 | 404.3 |
| I-12 | Nsc—Asp(OtBu)—OH | 3 | −12.7° | 72–75 | 0.64 | 0.38 | 447.44 | 447.2 |
| I-13 | Nsc—Gln(OtBu)—OH | 3 | −17.0° | 94–96 | 0.67 | 0.38 | 461.47 | 461.4 |
| I-14 | Nsc—Lys(Boc)—OH | 3 | −11.8° | 110–112 | 0.62 | 0.35 | 504.54 | 505.9 |
| I-15 | Nsc—Tyr(tBu)—OH | 3 | −6.3° | 82–84 | 0.68 | 0.44 | 495.53 | 495.2 |
| I-16 | Nsc—Trp—OH | 3 | −14.7° | 188–190 | 0.53 | 0.33 | 462.46 | 461.7 |
| I-17 | Nsc—Cys(Trt)—OH | 3 | +22.3° | 108–110 | 0.75 | 0.52 | 621.71 | 619.3 |
| I-18 | Nsc—His(Trt)—OH | 3 | +5.0° | 112–115 | 0.42 | 0.1 | 655.71 | 656.8 |
| I-19 | Nsc—Arg(Mts)—OH | 3 | −4.0° | 115–120 | 0.25 | 0.05 | 615.68 | 614.4 |
| I-20 | Nsc—Asn(Xan)—OH | 4 | +2.7° | 198–200 | 0.43 | 0.25 | 570.56 | 568.8 |
| I-21 | Nsc—Gln(Xan)—OH | 4 | −13.7° | 155–158 | 0.58 | 0.23 | 584.58 | 582.9 |
| I-22 | Nsc—Cys(Acm)—OH | 2 | −31.0° | 124–126 | 0.17 | 0.05 | 450.47 | 451.2 |
| I-23 | Nsc—Pro—OH | 2 | −31.5° | 115–117 | 0.53 | 0.37 | 371.35 | 371.3 |

EXAMPLE 6

Solid Phase Synthesis of Dodecapeptide
Ala-Ser-Ser-Thr-Ile-Ile-Lys-Phe-Gly-Ile-Asp-Lys a) Insertion of anchor group into polymeric carrier To 250 mg of aminomethylated styerne-1% divinylbenzene copolymer(1.0 meq. $NH_2$/g)in 3 ml of DMF 0.75 mmol -continued

| | |
|---|---|
| | 0.5 mmol:1-hydroxybenzotriazole, 0.5 mmol; N-methyl-morpholine, 0.75 mmol; DMF, 2 ml; 60 min (90min for NSC—Ile—OH). |
| 5. Wash: | DMF, 5 × (4 ml; 1 min) |

$N_\alpha$-Nsc-amino acids were introduced into synthetic cycles in the following oredr. Nsc-Asp(OtBu)-OH, Nsc-Ile-OH, Nsc-Gly-OH, Nsc-Phe-OH, Nsc-Lys(Boc)-OH, Nsc-Ile-OH, Nsc-Ile-OH, Nsc-Thr(tBu)-OH, Nsc-Ser(tBu)-OH, Nsc-Ser(tBu)-OH, Nsc-Ala-OH.

After the assembly of the target amino acid sequence the peptidyl-polymer was treated with 33% piperidine/DMF(4 ml)for 20 min, then washed with DMF, dichloromethane, ethanol, ether and finally, with hexane.

d) Deblocking and purification

The peptidyl-polymer was shaken with 5 ml of 50% trifluoroacetic acid in 1,2-dichloroethane for 60 min at room temperature. Polymer was filtered off, washed with 5 ml of 50% trifluoroacetic acid in 1,2-dichloroethane, and combined washings were diluted with 100 ml of ice-cold anhydrous ether. Precipitate was filtered off, washed with ether and dried in vacou, giving 170 mg of crude dodecapeptide(purity 70% by analytical reversed phase high performance liquid chromatography).

Crude dodecapeptide was dissolved in 3 ml of 1M aqueous acetic acid and was chromatographed on the 1.5×70 cm column packed with TSK HW-40F(Merck, Darmstadt, Germany), equilibrated and eluted with the same buffer. Fractions contained pure peptide were pooled and lyophilized. Final yield off the target dodecapeptide was 104 mg(41%), purity more than 95% as estimated by analytical reversed phase high performance liquid chromatography. Amino acid composition(after 6N HCl hydrolysis, 110° C., 24 and 48 hrs): Asp 1.02(1); Ser 1.84(2); Thr 0.93(1): Glu 0.94(1); Gly 1.03(1); Ala 1.00(1); Ile 2.78(3); Lys 2.04(2).

What is claimed is:

1. $N_\alpha$-2-(4-nitrophenylsulfonyl)ethoxycarbonyl-amino acids having the general formula:

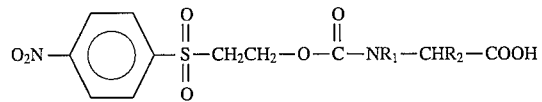

wherein $R_1$ represents hydrogen atom, and $R_2$ represents hydrogen, methyl, isopropyl, 1-methylpropyl, 2-methylpropyl, tert-butoxymethyl, 1-tert-butoxyethyl, 2-methylthioethyl, benzyl, carboxamido-methyl, 2-carboxamidoethyl, tert-butoxycarbonylmethyl, 2-(tert-butoxycarbonyl)ethyl, 4-(tert-butoxycarbomido)butyl, 4-tert-butoxybenzyl, indolyl-3-methyl, S-(triphenylmethyl)thiomethyl, 1-(triphenylmethyl)imidazolyl-4-methyl, 3-($N^G$-mesitylenesulfonyl)guanidinopropyl, N-xanthylcarboxamidomethyl, 2-(N-xanthylcarboxamido)ethyl or S-(acetamidomethyl)thiomethyl;

or $R_1$ and $R_2$ together represent propylene radical.

2. A method for preparing of compounds according to the claim 1 comprising reacting amino acid of the general formula $$HNR_1—CHR_2—COOH$$

wherein $R_1$ and $R_2$ represent radicals according to the claim 1, with 2-(4-nitrophenylsulfonyl)ethoxycarbonyl chloroformate in mixed aqueous-organic solvent in the presence of base.

3. A method for preparing of compounds according to the claim 1 comprising:

a) converting of amino acid of the general formula $$HNR_1—CHR_2—COOH$$

wherein $R_1$ and $R_2$ represent radicals according to the claim 1, into O,N-trimethylsilylated derivatives;

b) reacting of said O,N-trimethylsilylated derivatives derivatives with 2-(4-nitrophenylsulfonyl)ethoxycarbonyl chloroformate in aprotic solvent in the presence of base with subsequent hydrolysis.

4. A method for preparing of compounds according to the claim 1, wherein $R_1$ represents hydrogen atom, and $R_2$ represents N-xanthylcarboxamidomethyl or 2-(N-xanthylcarboxamido)ethyl, comprising reacting of compounds according to the claim 1, wherein $R_1$ represents hydrogen atom, and $R_2$ represents carboxamidomethyl or 2-(carboxamido)ethyl, with xathydrol in organic solvent in the presence of acid.

* * * * *